(12) United States Patent
Merchant

(10) Patent No.: US 6,616,696 B1
(45) Date of Patent: Sep. 9, 2003

(54) MODULAR KNEE REPLACEMENT SYSTEM

(76) Inventor: Alan C. Merchant, 124 Marvin Ave., Los Altos, CA (US) 94022

( * ) Notice: Subject to any disclaimer, the term of this patent is extended or adjusted under 35 U.S.C. 154(b) by 0 days.

(21) Appl. No.: 09/148,110

(22) Filed: Sep. 4, 1998

(51) Int. Cl.⁷ .................................................. A61F 2/42
(52) U.S. Cl. .................... 623/20.18; 623/20.15
(58) Field of Search .................. 623/20.15, 20.18, 623/20.19, 20.2

(56) References Cited

U.S. PATENT DOCUMENTS

| | | |
|---|---|---|
| 3,878,566 A | 4/1975 | Bechtol .................. 3/1.91 |
| 4,151,615 A | 5/1979 | Hall |
| 4,219,893 A | 9/1980 | Noiles |
| 4,240,162 A | 12/1980 | Devas |
| 4,301,553 A | 11/1981 | Noiles |
| 4,309,778 A | 1/1982 | Buechel et al. |
| 4,340,978 A | 7/1982 | Buechel et al. |
| 4,470,158 A | 9/1984 | Pappas et al. |
| 5,007,933 A | 4/1991 | Sidebotham et al. |
| 5,330,532 A | 7/1994 | Ranawat |
| 5,549,686 A | 8/1996 | Johnson et al. |
| 5,556,433 A | 9/1996 | Gabriel et al. |
| 5,609,640 A | 3/1997 | Johnson |
| 5,639,279 A | 6/1997 | Burkinshaw et al. |
| 5,755,803 A | 5/1998 | Haines et al. |
| 5,782,925 A | 7/1998 | Collazo et al. |
| 5,788,700 A | 8/1998 | Morawa et al. |
| 5,824,098 A | 10/1998 | Stein |
| 5,871,539 A | 2/1999 | Pappas ...................... 623/20 |
| 5,871,540 A | 2/1999 | Weissman et al. |
| 5,928,286 A | 7/1999 | Ashby et al. |

FOREIGN PATENT DOCUMENTS

| | | |
|---|---|---|
| DE | 4310968 A1 | 10/1994 |
| EP | 0582514 A1 | 8/1993 |
| EP | 0307654 B1 | 1/1994 |
| FR | 2594323 A1 | 2/1986 |
| FR | 2700260 A1 | 1/1993 |
| WO | WO 97/25006 | 7/1997 |

OTHER PUBLICATIONS

DePuy Inc., "New Jersey LCS Total Knee System," (1994) 20 pages.
Richards Technical Publication, "Resurfacing of the Patello–Femoral Joint," (1980) 16 pages.
Waldemar Link, "Lubinus Total Pattella Glide Replacement Prosthesis," (1978) 15 pages.
DePuy Inc., "New Jersey LCS Total Knee System," (1994) 55 pages, Barry et al.
Patella II, "Patello–Femoral Replacement," (Undated) 10 pages.
A.J. Cepulo, et al., "Mechanics of Patello–Femoral Replacement," (Undated) 4 pages.

(List continued on next page.)

Primary Examiner—Bruce Snow
(74) Attorney, Agent, or Firm—Townsend and Townsend and Crew LLP

(57) ABSTRACT

A trochlear implant for a prosthetic knee, a prosthetic knee system and a method for using the prosthetic knee system are disclosed. The trochlear implant mounts to the knee end of a femur and cooperates with a patellar implant mounted to the back side of a patella. The patellar implant is a component of a prosthesis including a femoral implant for replacing the knee end of the femur. The trochlear implant has an articulation surface shaped to slidably receive a portion of the patellar implant. The articulation surface is substantially similar in shape to a portion of a surface of the femoral implant such that the patellar implant is capable of being used with the femoral implant and the trochlear implant.

10 Claims, 10 Drawing Sheets

OTHER PUBLICATIONS

Patella I–II–III, "Surgical Techniques of the Richards Patello–Femoral Replacement Systems," (1976) 35 pages.

Johnson & Johnson Orthopaedics, "Primary Cruciate–Retaining Procedure/Primary Cruciate–Substituting Procedure," (Undated) 5 pages.

Intermedics Orthopedics, Inc., "Natural–Knee Family," (Undated) 2 pages.

Insall/Burstein II, "Modular Knee System," (Undated) 5 pages.

DePuy Medinov, "Autocentric II," (Undated) 6 pages.

Howmedica Products: Kinemax® Plus total Knee System. A Fully Integrated System, total of 2 pages. [online] [retrieved on Jul. 29, 2002]. Retrieved from the Internet <http://www.howost.com/howmedica/products/frames/prod16a.htm>.

Howmedica Products: Kinemax® Plus total Knee System. Kinemax Plus: Pure Gold, total of 1 page. [online] [retrieved on Jul. 29, 2002]. Retrieved from the Internet <http://www.howost.com/howmedica/products/frames/prod16.htm>.

Howmedica Products: Kinemax® Plus total Knee System. Optimized Articular Surfaces: Conformity Without Constraint, total of 2 pages. [online] [retrieved on Jul. 29, 2002]. Retrieved from the Internet <http://www.howost.com/howmedical/products/frames/prod16c.htm>.

Howmedica Products: Kinemax® Plus total Knee System. Outstanding Clinical Results: The Proven Path—From the Past to the Future, total of 2 pages [online] [retrieved on Jul. 29, 2002]. Retrieved from the Internet <http://www.howost.com/howmedica/products/frames/prod16e.htm>.

Howmedica: MRS total of 1 page. [online] [retrieved on Jul. 29, 2002] Retrieved from the Internet <http://www.howost.com/howmedica/mrs/text.htm>.

Howmedica: MRS. Distal Femur Diagram, total of 1 page. [online] [retrieved on Jul. 29, 2002 ]. Retrieved from the Internet <http>.

Howmedica: MRS. Exploded View of Kinematic Rotating Hinge Components total of 1 page. [online] [retrieved on Jul. 29, 2002]. Retrieved from the Internet http://www.howost.com/howmedia/mrs/distalfemur3a.htm>.

Howmedica: MRS. Femoral Condyle, total of 1 page. [online] [retrieved on Jul. 29, 2002]. Retrieved from the Internet <http://www.howmost.com/howmedica/mrs/disatalfemur1.htm>.

Stryker Corporation Overview. Stryker, p. 1–26 [online] [retrieved on Sep. 19, 2002]. Retrieved from the internet <http://www.strykercorp.com/pdfs/product_brochure.pdf>.

TKA Meta Site. Stryker ® Howmedica Osteonics. Total Knee Arthroplasty, total of 1 page. [online] [retrieved on Jul. 29, 2002]. Retrieved form the Internet <http://www.howost.com/osteonics/knees/welcome/knee.html>.

MODULAR KNEE REPLACEMENT SYSTEM

BRIEF DESCRIPTION OF THE INVENTION

The present invention relates in general to a modular knee replacement system for a prosthetic joint, and more particularly to a system including a trochlear implant.

BACKGROUND OF THE INVENTION

A knee joint connects three bones: the femur (thigh bone), the tibia (leg bone), and the patella (knee cap). Either through disease, injury, or pre-mature wear from malalignment, the knee joint can be damaged, and all or portions of the damaged joint surfaces may need to be replaced with a prosthesis. The most common prosthetic knee is referred to as a "total knee replacement" system because all knee joint surfaces are replaced. Typically the total knee replacement system includes a patellar prosthesis or implant, a femoral prosthesis or implant and a tibial, prosthesis or implant.

Different portions of the knee are referred to as compartments. For example, each condyle (rounded end of the femur) is a separate compartment. Other prostheses, called "unicompartmental" replacements, can be used when only the medial (toward the body's midline) compartment or the lateral (away from the body's midline) compartment of the femoral-tibial surface needs to be replaced. The unicompartmental replacement systems have femoral and tibial prostheses but do not include a patellar implant. Currently available unicompartmental implant systems are designed to be modular and work with their total knee counterparts from the same manufacturer with respect to using the same instruments and same bone contour. When these unicompartmental prosthetic systems need to be replaced with a total knee system, both the femoral and tibial implants must be removed.

Less frequently, the surface of the knee joint compartment between the patella If, and the groove on the front of the femur the (trochlea) requires replacement. Several prosthetic implants are available which replace this part of the knee joint and are called "total patello-femoral" prostheses or implants. Typically the total patello-femoral prostheses have a patellar implant that is installed on the patella and another implant which replaces the portion of the femur which contacts the patella(the trachlea).

However, there is no total patello-femoral prosthetic system which is modular with any total knee system. Therefore, if a total patello-femoral prosthesis has been implanted, and because of further deterioration in the rest of the knee (possibly years later), during a then second operation both the trochlear implant and the patellar prosthesis must be removed even though the patellar prosthesis is functioning well. The only reason for removing said patellar prosthesis is that its articular surface would not now match or articulate smoothly with the new femoral prosthesis being implanted.

A prosthesis system which does not require replacement of the patella implant when replacing the patello-femoral prosthesis with a total knee prosthesis is desirable. In particular, a trochlear implant which is applied to the surface of the trochlear groove of the femur and which cooperates with the components of the selected total knee implant is desirable.

OBJECTS AND SUMMARY OF THE INVENTION

It is a primary object of the present invention to provide a prosthesis system which does not require replacement of the patella implant when replacing the trochlear implant with a full femoral implant.

It is another object of the present invention to provide a trochlear implant which cooperates with the components of the selected total knee implant system.

A more general object of the present invention is to provide a trochlear implant for a prosthetic joint that reduces the amount of bone removed for the implant.

It is yet another object of the present invention to provide a modular joint replacement system having interchangeable components.

In summary the present invention provides a prosthetic knee of the type which includes a femoral implant or a trachleas implant and a patellar implant. The femoral implant and the patellar implant have bearing surfaces that articulate with each other when the femoral implant and patellar implant move relatively. The trochlear implant has an articulation surface shaped to articulate with a portion of the bearing surface of the trochlear implant of the patellar implant. The articulation surface is substantially similar in shape to a portion of the bearing surface of the femoral implant such that the patellar implant is usable with either the femoral implant or the trochlear implant.

The present invention also provides a trochlear implant for use in a prosthetic knee. The trochlear implant mounts to the knee end of a femur and cooperates with a patellar implant mounted to the back side of a patella. The patellar implant is a component of a prosthesis system including a femoral implant for replacing the entire knee end of the femur. The trochlear implant has an articulation surface shaped to slidably receive a portion of the patellar implant. The articulation surface is substantially similar in shape to a portion of a surface of the femoral implant such that the patellar implant is capable of being used with either the femoral implant or the trochlear implant.

In addition, the present invention provides a method of knee replacement using a prosthetic knee system. A trochlear implant and a patellar implant are provided. The patellar implant cooperates with the trochlear implant and a femoral implant. The trochlear implant has an articulation surface shaped to slidably receive a portion of the patellar implant. The articulation surface is substantially similar in shape to a portion of a load bearing surface of a femoral implant. The patellar implant is installed in a patella in a knee. The trochlear implant is installed in the trochlear groove in the knee end of a femur bone.

BRIEF DESCRIPTION OF THE DRAWINGS

The invention will be clearly understood from a reading of the following description in conjunction with the accompanying drawings.

DETAILED DESCRIPTION OF THE PREFERRED EMBODIMENTS

Figures 1, 2:
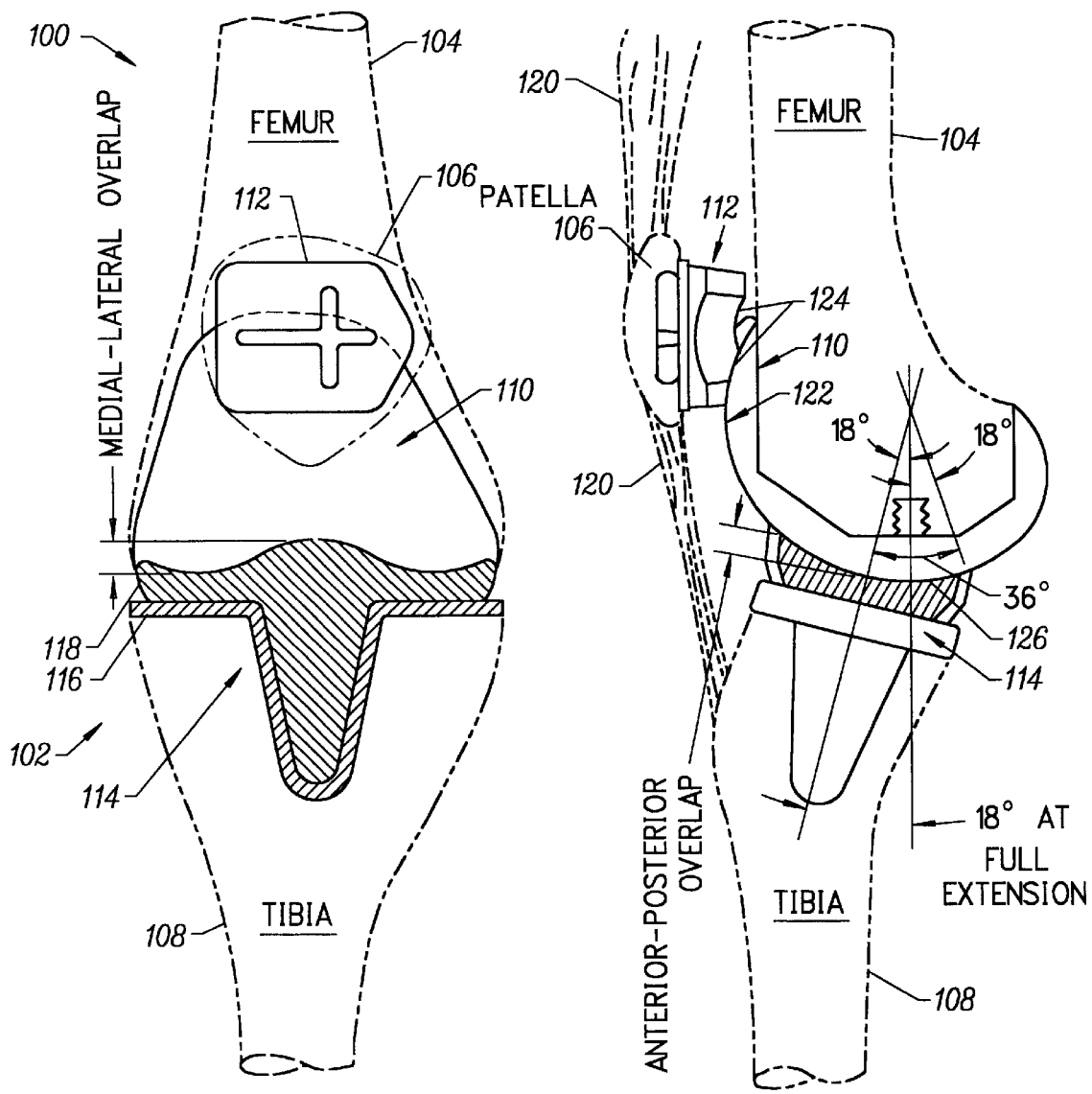
FIG. 1 is a front view of an installed prior art total knee prosthesis.
FIG. 2 is a side view of the installed prior art total knee prosthesis of FIG. 1.

In FIG. 1, a prosthetic knee implant 100 suitable for use with the present invention is installed in a human knee 102. The knee 102 has a femur 104, a patella 106 and a tibia 108. The prosthetic knee 100 includes a femoral implant 110, a patellar implant 112 and an optional tibial implant 114. The tibial implant 114 has a tibial platform component 116 and a tibial bearing component 118.

The patellar implant 112 is shaped to mate with the femoral implant 110. The tibial implant 114, and in particular the tibial bearing component 118, is shaped to mate with the femoral implant 110. The femoral implant 110 is shaped to slidably receive the patellar implant 112 and the tibial implant 114.

FIG. 2 is a side view of the installed prosthetic knee of FIG. 1 and also shows a tendon 120 that attaches the muscles to the patella 106. The femoral implant 110 and the patellar implant 112 have bearing surfaces, 122 and 124, respectively. When the femoral implant and patella implant move relative to each other, the bearing surfaces 122 and 124 allow the femoral implant 110 and patella implant 112 to slidably engage. The tibial implant 114 also has a bearing surface 126 that slidably engages another portion of the femoral bearing surface 122 when the femur 104 and tibia 108 move relative to each other.

Figure 3:
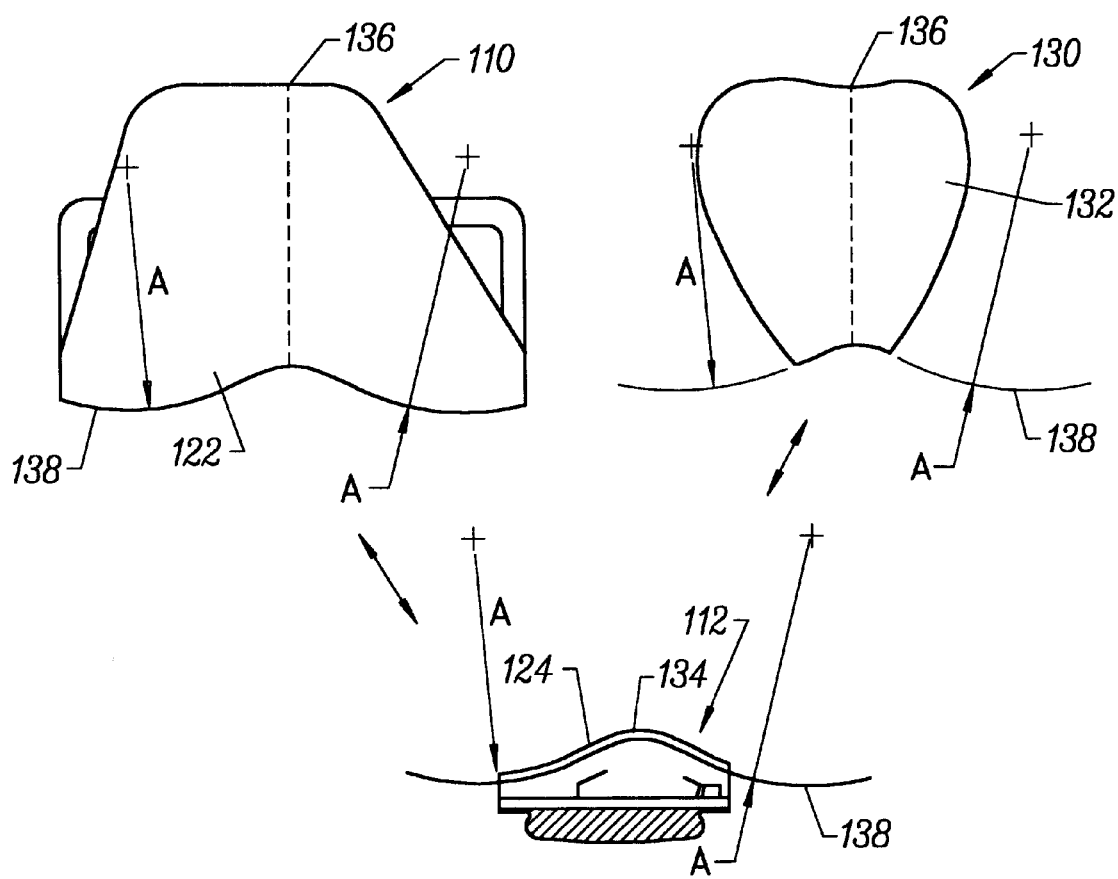
FIG. 3 is an exploded front view of the components of the prosthetic knee implant system of the present invention.

As shown in FIG. 3, the prosthetic knee system of the present invention includes a femoral implant 110, a patellar implant 112 and a trochlear implant 130. The trochlear implant 130 has an articulation surface 132 shaped to slidably receive a portion of the bearing surface 124 of the patellar implant 112. The patellar implant 112 has an apex 134 that aligns with a longitudinal axis 136 forming a trochlear groove in both the femoral implant 110 and the trochlear implant 130.

A noteworthy aspect of the invention is that the articulation surface 132 of the trochlear implant 130 is substantially similar in shape to a portion of the femoral bearing surface 122 of the femoral implant 110. Therefore, the patellar implant 112 is usable with both the femoral implant 110 and the trochlear implant 130. When a patient's remaining joint surface deteriorates to the point where the physician needs to replace the trochlear implant 130 with the femoral implant 110, the patient's patella is not subjected to additional bone loss and trauma because the existing patellar implant 112 is usable with the new femoral implant 110.

Fundamental differences among knee prostheses are found in the nature of the articulation or bearing surfaces. There are two basic types of articulation surfaces: those surfaces with theoretical line or point contact (referred to as incongruent contact), and those surfaces with area contact (referred to as congruent contact). Those surfaces with congruent contact more closely resemble the human body.

In a preferred embodiment, the articulation surface 138 of the trochlear implant 130 has a shape that substantially congruently engages the patellar implant 112. In an alternate embodiment, the articulation surface 132 of the trochlear implant 130 is shaped to provide substantially point contact with the patellar implant 112. In another alternate embodiment, the articulation surface 132 of the trochlear implant 130 is shaped to provide substantially line contact with the patellar implant 112. In other embodiments, the articulation surface 132 of the trochlear implant 130 is shaped to provide a combination of congruent and line contact with the patellar implant 112.

In one embodiment, the trochlear implant 130 is asymmetrical about the longitudinal axis 136 for installation in either a right knee or a left knee. In FIG. 3, the trochlear implant 130 is for installation in a right knee. In an alternate embodiment, the trochlear implant 130 is symmetrical about the longitudinal axis and can be installed in either the right knee or the left knee.

In a preferred embodiment, the bearing surface of the femoral implant 110, the bearing surface of the patellar implant 112 and the articulation surface of the trochlear implant 130 are aligned to and are generated by a common generation curve 138, FIG. 3. Alternately, the articulation surface of the trochlear implant 130 is shaped to receive and engage a substantially spherical, dome-shaped patellar implant 112.

The trochlear implant 130 may be made of cast cobalt-chrome-molybdenum and the articulation surface 132 is polished. Alternately, the trochlear implant 130 is made of cobalt-chrome, stainless steel or other suitable metal alloy. In another alternative embodiment, the trochlear implant 130 is made of a ceramic. In yet another embodiment, the trochlear implant 130 is made of titanium. In another alternate embodiment, a surface treatment is applied to harden and/or smooth the articulation surface of the trochlear implant 130. In particular, a trochlear implant 130 made of titanium is treated to harden and smooth the articulation surface.

Figure 4:
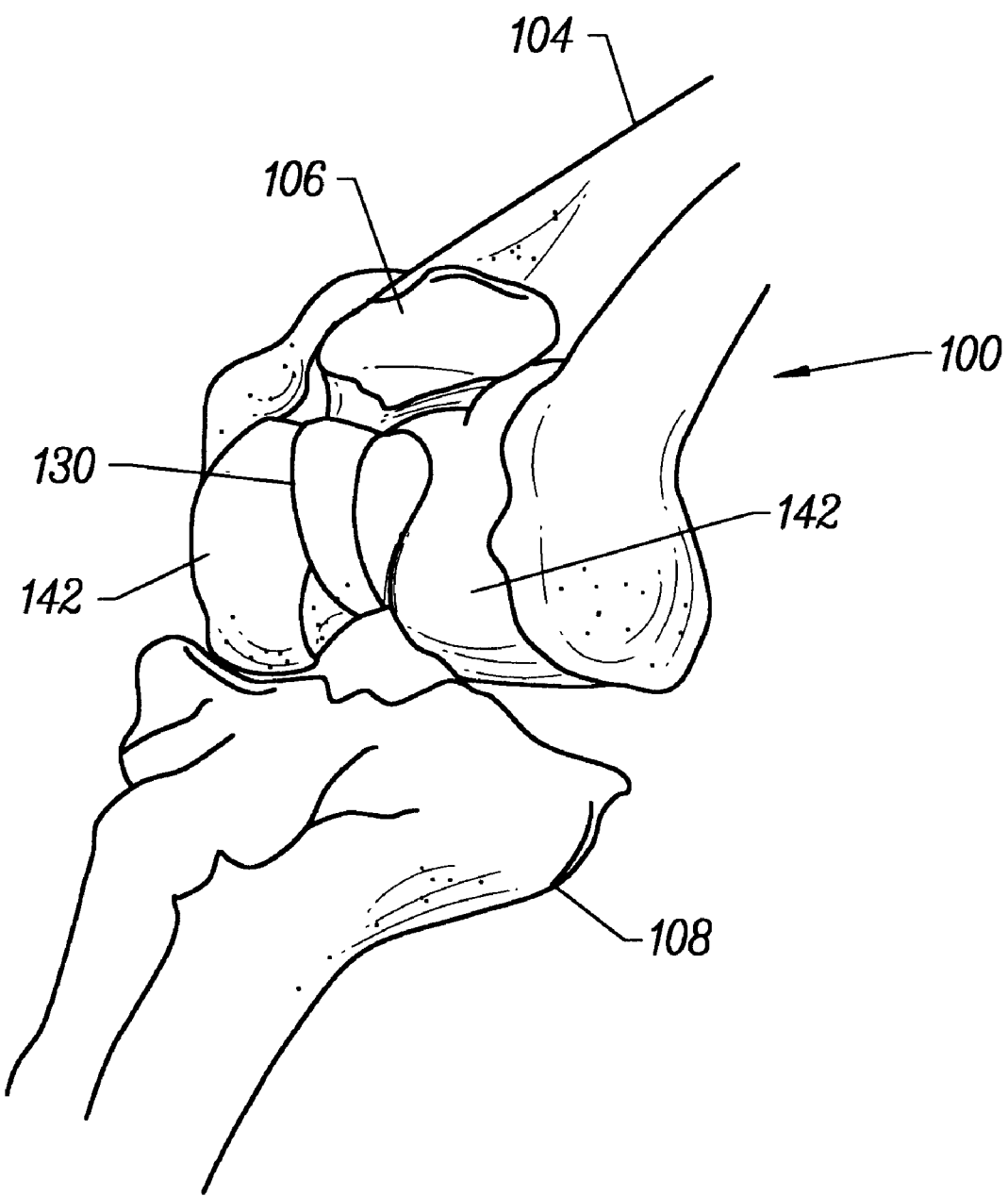
FIG. 4 is a perspective view of one embodiment of the trochlear implant of FIG. 3 installed in a human knee.

The trochlear implant 130 is installed in the trochlear groove between the condyles 142 of a knee-end of a femur 104 in a human knee 100, FIG. 4. In this embodiment, the trochlear implant 130 does not contact the tibia 108 or a tibial implant. In an alternate embodiment, the trochlear implant 130 can contact the tibia 108 or the tibial implant.

Figure 5:
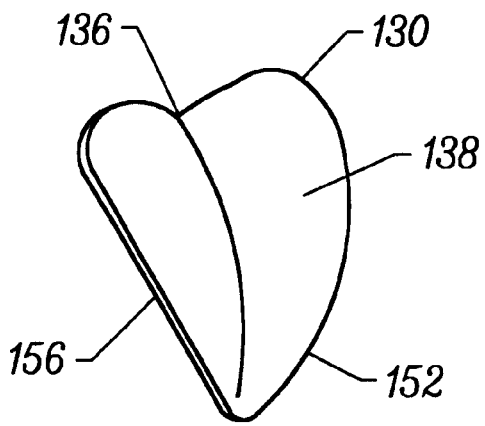
FIG. 5 is a perspective view of an embodiment of the trochlear implant of the present invention suitable for installation in a left knee.
Figure 6:
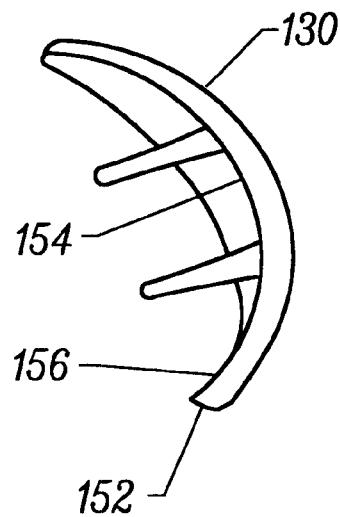
FIG. 6 is a side view of the trochlear implant of FIG. 5.
Figure 7:
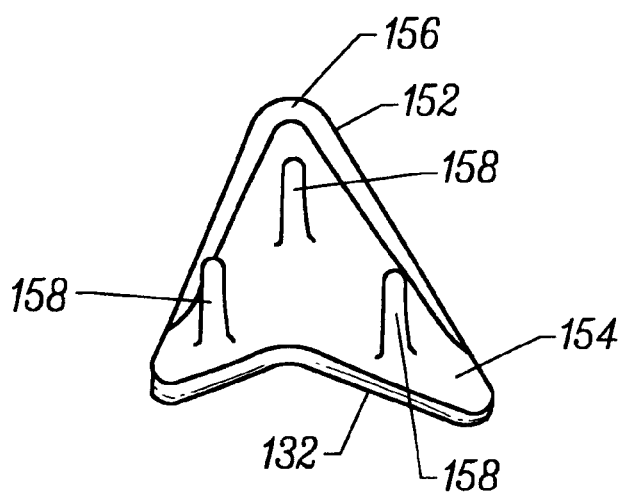
FIG. 7 is a bottom view of the trochlear implant of FIG. 5.

Referring to FIGS. 5, 6 and 7, a peripheral edge 152 defines and forms the articulation surface 132 and a back surface 154. In FIG. 7, the back surface 154 has a cement retaining rim 156 extending along a portion of the back surface 154 and portion of the peripheral edge 152. Three fixation pins 158 project from the back surface 154. In one embodiment, the back surface 154 is textured. Alternately, the back surface 154 has a porous coating. In an alternate embodiment, no cement retaining rim 156 is provided. In another alternate embodiment, no fixation pins are provided. In yet another alternate embodiment, any number, such as one, two, or more than three, fixation pins 158 project from the back surface 154. Alternately the trochlear implant 130 is fixed to the femur using screws.

Figures 8, 9:
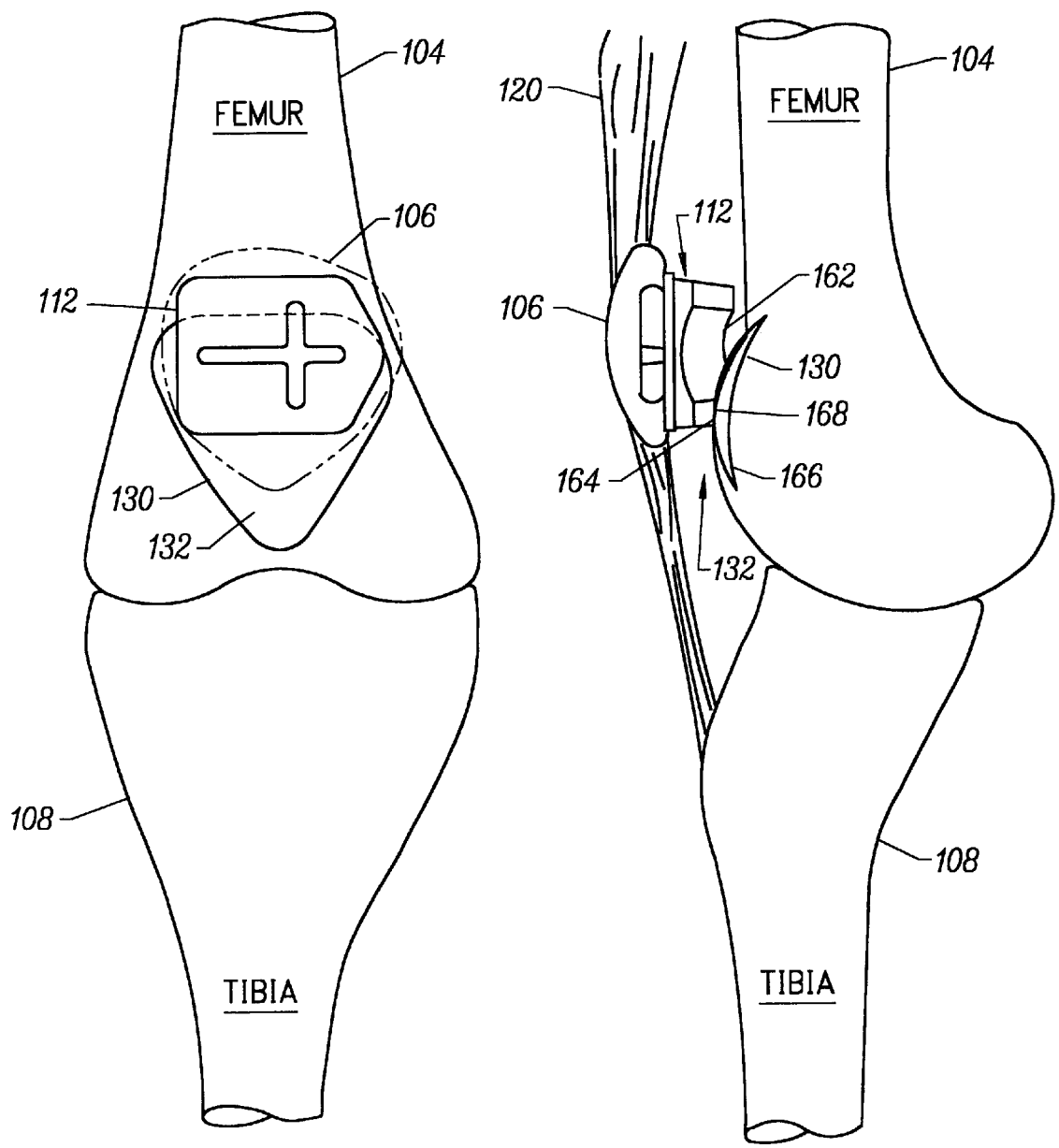
FIG. 8 is a front view of the trochlear implant of FIG. 5 installed in a human knee.
FIG. 9 is a side view of the trochlear implant of FIG. 5 installed in the human knee.

In FIGS. 8 and 9, the trochlear implant 130 of the present invention is shown in a human knee with the patellar implant 112. The trochlear implant 130 contacts the patellar implant 112 for a range of knee motion. Primary and secondary load bearing regions, 162 and 164, respectively, on the patellar implant 112 engage primary and secondary load bearing regions, 166 and 168, respectively, of the articulation region 132 of the trochlear implant 130 to produce substantially anatomical patella-femoral articulation. As shown in FIG. 9, at full extension of the leg and knee, the primary load bearing region 162 of the patellar implant 112 lifts off the primary load bearing region 166 of the trochlear implant 130, and the secondary load bearing region 164 of the patellar implant 112 slidably engages the secondary load bearing region 168 of the trochlear implant 130. In contrast, at moderate and full flexion, the primary load bearing region 162 of the patellar implant 112 slidably engages the primary load bearing region 166 of the trochlear implant 130.

In an alternate embodiment, at the extremes of knee motion, either when the knee is very straight or when the knee is extremely bent, the patellar implant 112 does not contact the trochlear implant 130. Preferably, the patellar implant 112 slidably engages the trochlear implant 130 from an angle of about 20° when the knee is almost straight to an angle of about 110° when the knee is bent.

Figure 10:
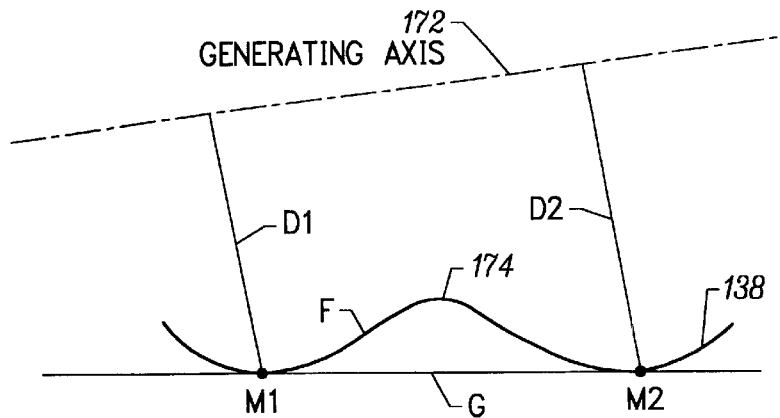
FIG. 10 is a diagram of a common generation curve used in a preferred embodiment of the trochlear implant of FIG. 3.

FIG. 10 shows the common generation curve 138 that is used to generate the shapes of the articulation and load bearing surfaces of the trochlear implant, femoral implant, patellar implant and tibial implant in a preferred embodiment of the present invention. The formation of the load bearing surfaces of the femur, patellar and tibial implants is described in detail in U.S. Pat. No. 4,470,158 to Pappas et al. which is incorporated herein by reference.

The primary and secondary load bearing regions of the articulation and load bearing surfaces are formed as surfaces of revolution and their shape is defined or generated by the common generation curve F 138. The shape of the load bearing or articulation surfaces is defined by rotating the common generation curve F 138 through a predetermined angle about the generating axis 172 at the same major generating radii D1 and D2 where D1 and D2 are equal to each other and also equal to a predefined radius. The peak 174 of the common generation curve F 138 forms the apex 134 (FIG. 3) of the patellar implant and the longitudinal axis 136 (FIG. 3) of the femoral implant and the trochlear implant.

Figure 11:
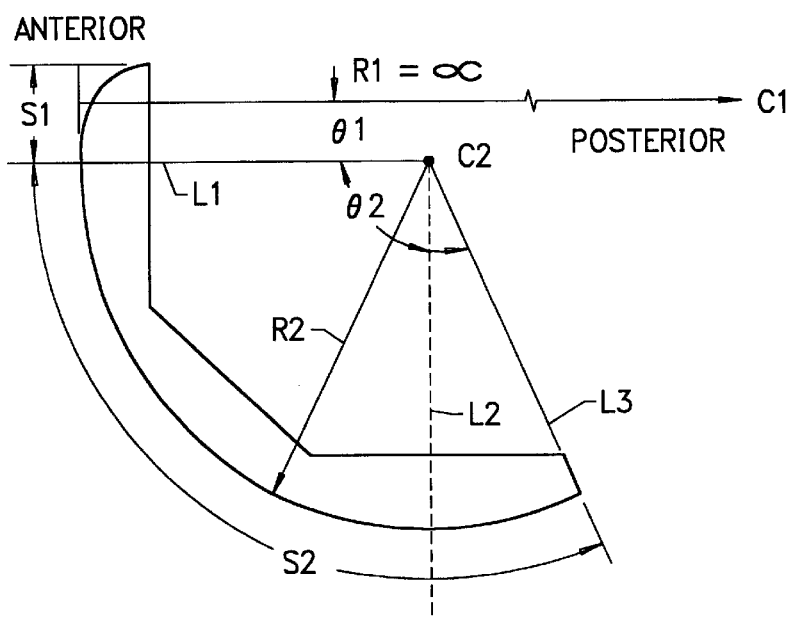
FIG. 11 is a diagram showing the rotation of the common generation curve of FIG. 10 to generate the segments of surfaces of revolution that define the shape of the articulation surface of the trochlear implant and that define the shape of the femoral load bearing surface of a femoral implant, and that also define the shape of a load bearing surface of the patellar implant.

FIG. 11 shows the segments S1 and S2 of the load bearing regions of the load bearing surface and articulation surface of the femoral implant and trochlear implant of the present invention, respectively. Segment S1 forms the secondary load bearing region 164, 168 (FIG. 9). Segment S2 forms the primary load bearing regions 162, 166 (FIG. 9) of the patellar implant and trochlear implant, respectively.

In particular, to generate the articulation region of the trochlear implant. The common generating curve 138 is rotated at an angle of θ1, equal to 0°, at a radial distance from generating axis C1 at ∞. In other words, the common generating curve 138 is substantially parallel to the line L1 for a distance of S1 or 0.314 inches. Tangent to line L1, the common generating curve 138 is rotated about generating axis C2 for an angle of θ2 at a radial distance of R2. In one embodiment, θ2 and R2 equal about 90° and 1.388 inches, respectively. The shape of the trochlear implant ends at line L2.

The load bearing regions of the patellar implant and femoral implant are generated in a similar manner. For the femoral implant, segment S1 is formed substantially parallel to the line L1 for a distance of 0.612 inches, and segment S2 is formed for an angle θ2 of 107.75° with R2 equal to 1.388 inches. Therefore, the trochlear implant load bearing regions 148, 146 (FIG. 9) formed with segments S1 and S2, respectively, substantially match the load bearing regions S1 and S2 of the femoral implant.

Figure 12:
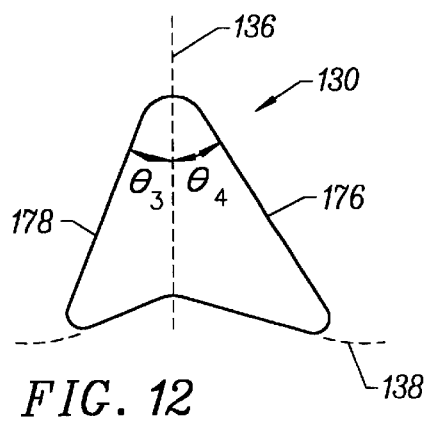
FIG. 12 is a bottom view of the trochlear implant of FIG. 5 showing the angles used to taper the peripheral edges.

Referring to FIG. 12, the trochlear implant 130 is tapered. To taper the trochlear implant 130, a portion of the common generation curve 138 is used and peripheral side edges 176, 178 of the trochlear implant 130 are formed at predetermined angles θ3 and θ4 with respect to the longitudinal axis 136. In one embodiment, the predetermined angles θ3 and θ4 are substantially equal to about 20° and 30°, respectively. In an alternate embodiment, θ3 and θ4 are the same.

Figure 13:
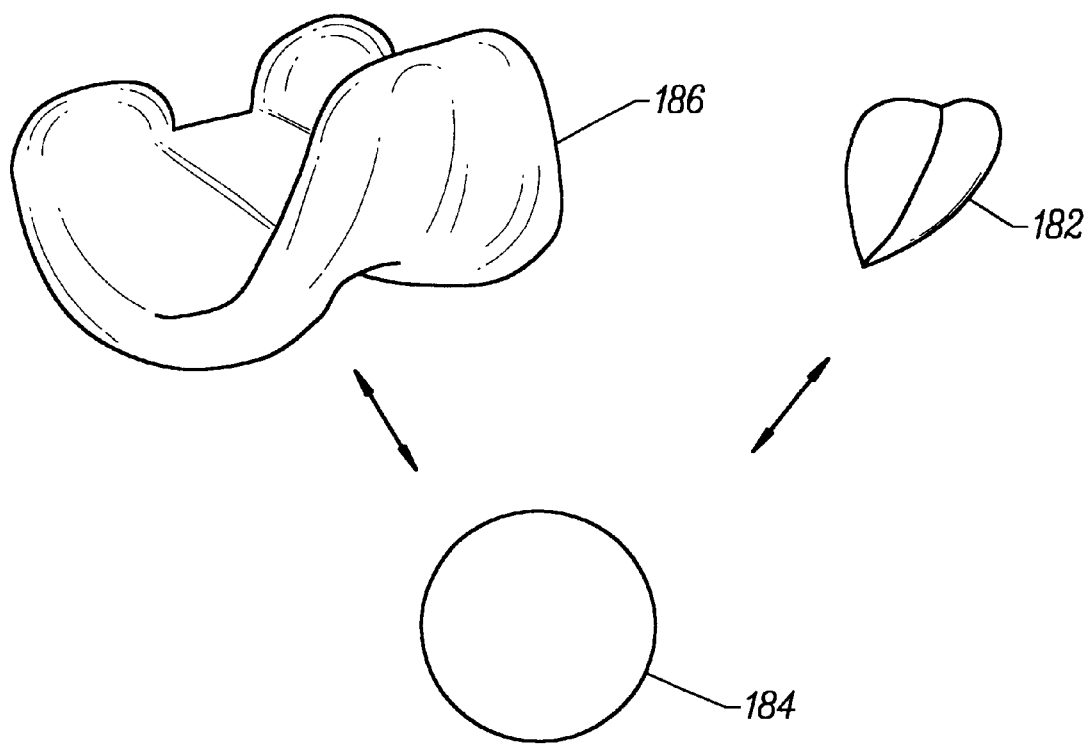
FIG. 13 is an exploded view of a second prosthetic knee system using another embodiment of the trochlear implant of the present invention.

FIG. 13 shows a second prosthetic knee system, such as the Johnson & Johnson "PRIMARY CRUCIATE-SUBSTITUTING" (P.F.C.) modular total knee system, with a second embodiment of the trochlear implant 182 of the present invention. A patellar implant 184 is usable with either the femoral implant 186 or the trochlear implant 182.

Figure 14:
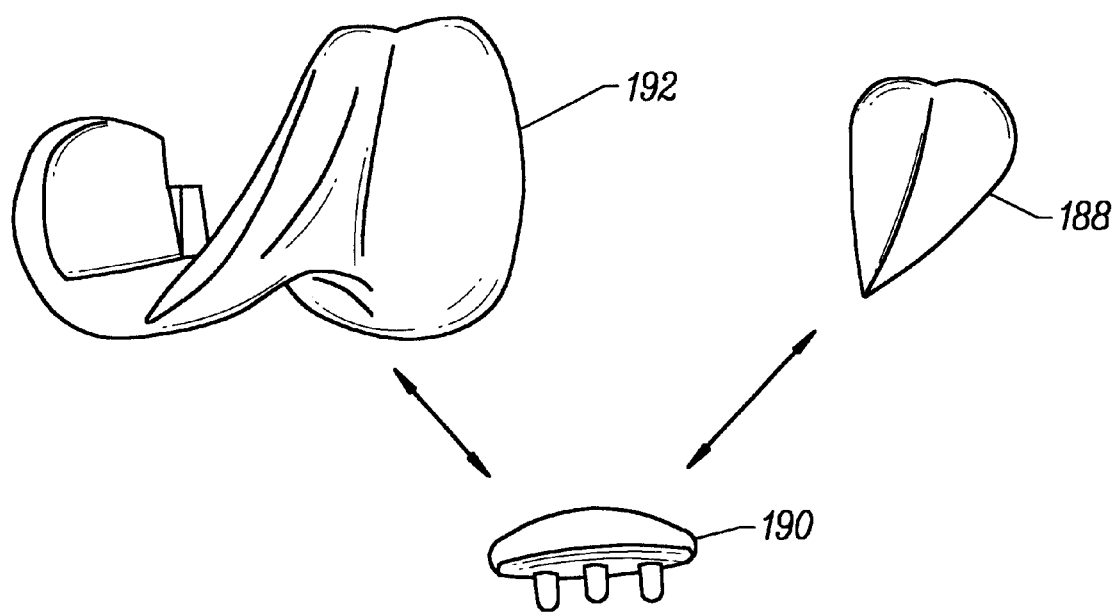
FIG. 14 is an exploded view of a third prosthetic knee system using yet another embodiment of the trochlear implant of the present invention.

FIG. 14 shows a third prosthetic knee system, such as the Intermedics "NATURAL-KNEE," with a third embodiment of the trochlear implant 188 of the present invention. A patellar implant 190 is usable with either a femoral implant 192 or the trochlear implant 188.

Figure 15:
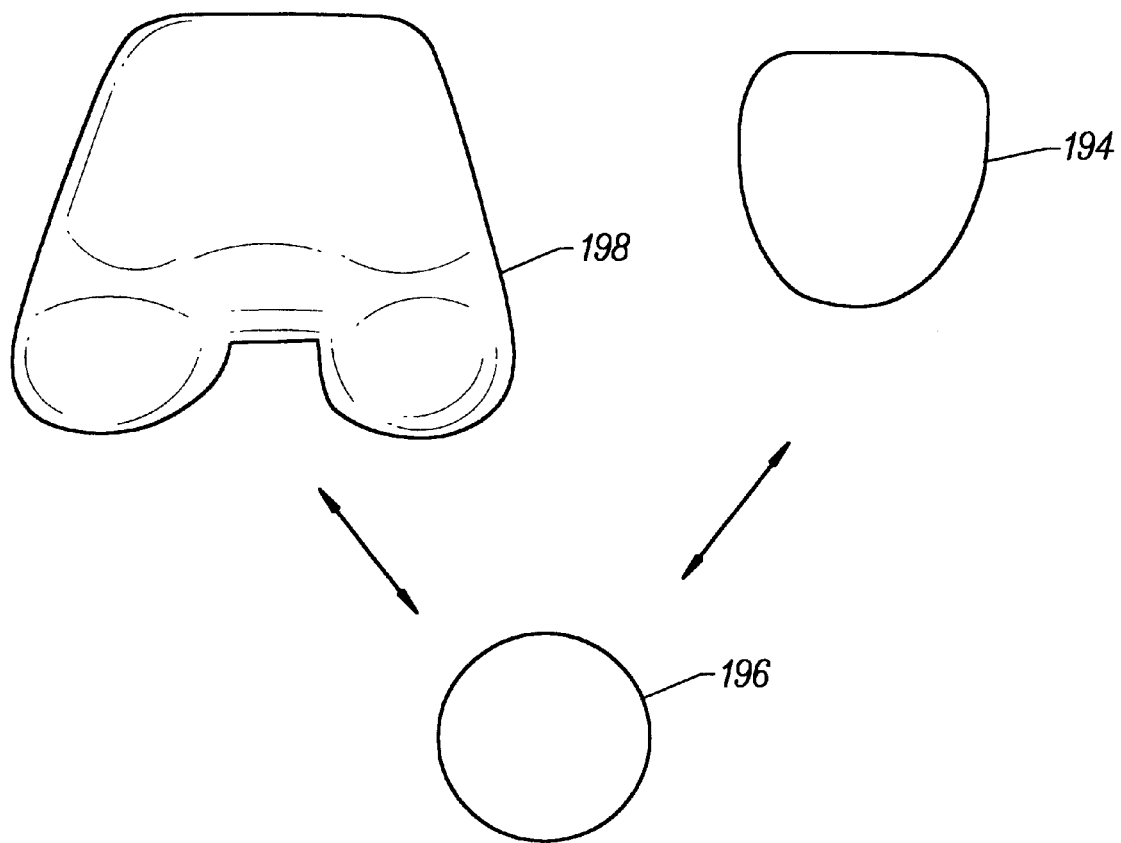
FIG. 15 is an exploded view of a fourth prosthetic knee system using another alternative embodiment of the trochlear implant of the present invention.

FIG. 15 shows a fourth prosthetic knee system, such as the Zimmer "Insall/Burstein (I/B) II" modular knee system, with a fourth embodiment of the trochlear implant 194 of the present invention. A patellar implant 196 is usable with either a femoral implant 198 or the trochlear implant 194.

Figure 16:
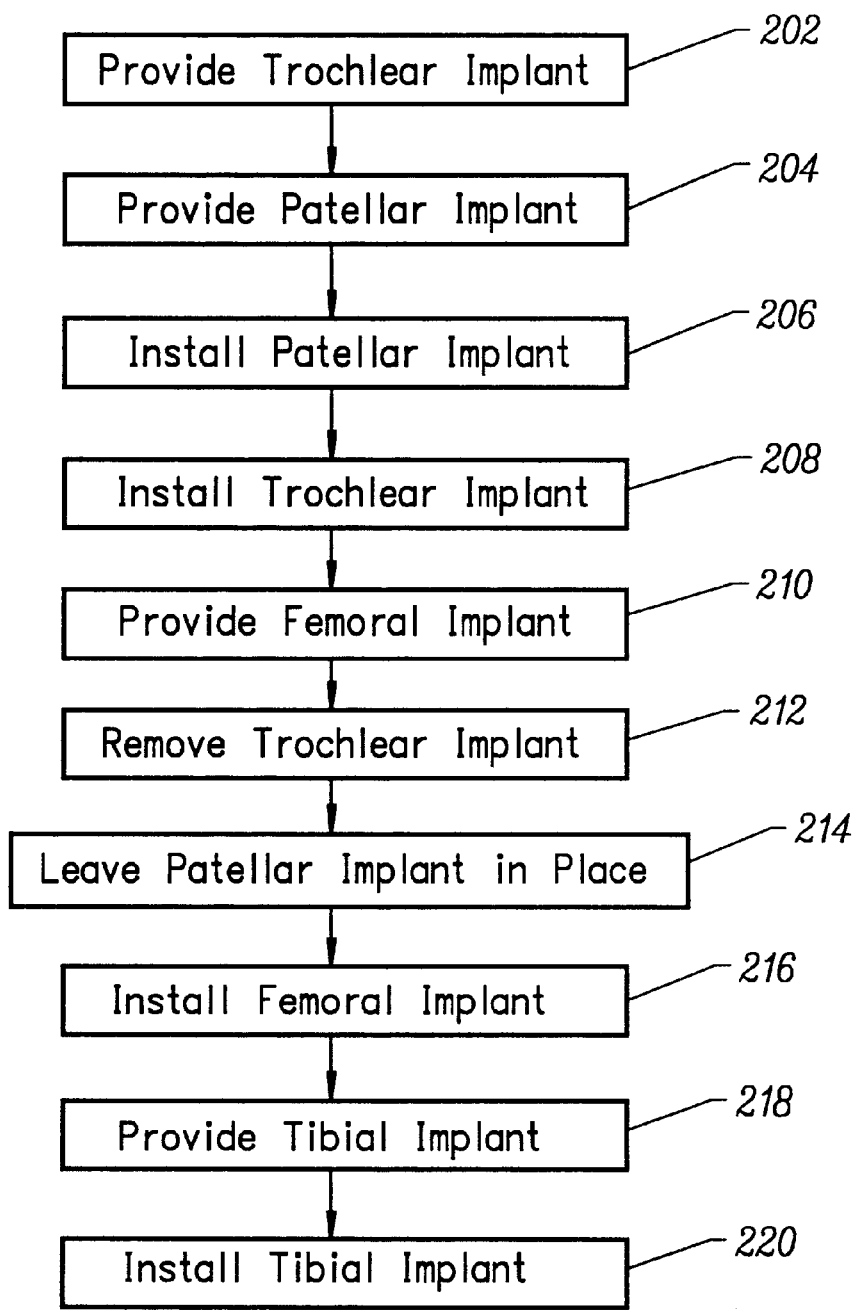
FIG. 16 is a flowchart of a method of knee replacement using the components of the prosthetic knee system of the present invention.

In FIG. 16, a flowchart of an embodiment of a method of knee replacement using the components of the prosthetic knee system is shown. In step 202, a trochlear implant of the present invention is provided, and in step 204, a patellar implant suitable for use with the present invention is also provided. In step 206, the patellar implant is installed in a patella in a knee. In step 208, the trochlear implant is installed in the trochlear groove in a knee-end of a femur bone.

When a patient's remaining joint surface deteriorates to the point where the trochlear implant needs to be replaced, in step 210 a femoral implant suitable for use with the trochlear implant is provided. The shape of the articulation surface of the trochlear implant and the shape of the load bearing surface of the femoral implant are substantially similar. In step 212, the trochlear implant is removed, and in step 214 the existing patellar implant is left in place in the patella. In an alternate embodiment, the patellar implant has a detachable load bearing surface, however, even in such patellar implants, the portion of the patellar implant that is attached to the patella bone remains in place.

In step 216, the surgeon installs the femoral implant in the knee-end of the femur bone. If the tibia portion of the knee also needs to be replaced, a tibial implant is also provided in step 218, and installed in step 220.

Thus, there has been provided a prosthetic knee system that allows the same patellar implant to be used with both a trochlear implant and a femoral implant. Therefore, when a patient's remaining joint surface deteriorates to the point where the physician needs to replace the trochlear implant with the femoral implant, the patient's patella is not subjected to additional bone loss and trauma because the existing installed patella implant is usable with the new femoral implant.

While the invention has been described in detail and with reference to specific examples, it will be apparent to one skilled in the art that various trochlear implant shapes can be made without departing from the spirit and scope of the present invention.

What is claimed is:

1. A prosthetic knee system comprising:
    a patellar implant implantable on the rear of the patient's patella, said patella implant having a bearing surface;
    a trochlear implant implantable on the knee end of a patient's femur, said trochlear implant having an articulation surface which engages the bearing surface of the patellar implant; and
    a femoral prosthesis implantable in the knee end of a patient's femur in place of the trochlear implant, said femoral prosthesis having a bearing surface which engages the bearing surface of the patellar implant and a prosthetic tibial component, wherein the contour of the bearing surface of the femoral prosthesis is shaped identically to a portion of the articulation surface of the trochlear implant which engages the bearing surface of the patellar implant;
    wherein the bearing surface of the patellar implant is shaped to provide area contact and congruent engagement with both the articulation surface of the trochlear implant and the bearing surface of the femoral prosthesis.

2. A prosthetic knee system as in claim 1 wherein said articulation surface of said trochlear implant and the bearing surface of the femoral prosthesis each have a groove for engaging the patellar implant.

3. A prosthetic knee system as in claim 1 wherein said trochlear implant and said femoral prosthesis are symmetrical about a longitudinal axis for installation in either of a right knee and a left knee.

4. A prosthetic knee system as in claim 1 wherein said trochlear implant and said femoral prosthesis are asymmetrical about a longitudinal axis for installation in only one of a right knee or a left knee.

5. A prosthetic knee system as in claim 1 wherein said trochlear implant is made of cobalt-chrome-molybdenum.

6. A prosthetic knee system as in claim 1 wherein said trochlear implant comprises:
    a back surface and a peripheral edge forming said articulation surface and a back surface; and
    said back surface including a cement retaining rim extending along at least a portion of the back surface and at least a portion of said side edge.

7. A prosthetic knee system as in claim 1 wherein said trochlear implant comprises:
    a back surface and sides; and
    at least one fixation pin projecting from said back surface.

8. The prosthetic knee system as in claim 1 wherein said articulation surface of said trochlear implant and said bearing surface of said femoral prosthesis are defined by rotating a common generation curve through a predetermined angle about a predetermined generating axis.

9. A prosthetic knee system as in claim 1 wherein said articulation surface of said trochlear implant and said bearing surface of said femoral prosthesis comprise a compound surface having a first lateral surface generated by moving said common generation curve for a first predetermined distance, said first lateral surface being laterally joined to a second lateral surface generated by rotating said common generation curve with a second radius for a predetermined angle.

10. A prosthetic knee system as in claim 1 wherein said articulation surface of said trochlear implant and bearing surface of said femoral prosthesis comprise a compound surface having a first surface that is laterally connected to a second surface, said compound surface being generated by a common generation curve, said first surface being generated by moving the common generation curve for a first predetermined distance, said second surface being generated by rotating said common generation curve at a predetermined radius for a predetermined angle.

* * * * *